(12) United States Patent
Hooven

(10) Patent No.: US 7,530,980 B2
(45) Date of Patent: May 12, 2009

(54) BIPOLAR TRANSMURAL ABLATION METHOD AND APPARATUS

(75) Inventor: Michael D. Hooven, West Chester, OH (US)

(73) Assignee: Atricure, Inc, West Chester, OH (US)

( * ) Notice: Subject to any disclaimer, the term of this patent is extended or adjusted under 35 U.S.C. 154(b) by 568 days.

(21) Appl. No.: 11/104,725

(22) Filed: Apr. 13, 2005

(65) Prior Publication Data

US 2005/0234444 A1 Oct. 20, 2005

Related U.S. Application Data

(60) Provisional application No. 60/561,937, filed on Apr. 14, 2004.

(51) Int. Cl.
*A61B 18/04* (2006.01)
(52) U.S. Cl. .......................................... 606/41; 606/32
(58) Field of Classification Search ................... 606/41, 606/32, 49, 50, 34
See application file for complete search history.

(56) References Cited

U.S. PATENT DOCUMENTS

| | | | |
|---|---|---|---|
| 1,127,948 A | 2/1915 | Wappler | |
| 2,004,559 A | 6/1935 | Wappler et al. | |
| 3,470,875 A | 10/1969 | Johnson et al. | |
| 3,630,207 A | 12/1971 | Kahn et al. ................. | 128/350 |
| 3,901,242 A | 8/1975 | Storz .......................... | 128/303 |
| 4,043,342 A | 8/1977 | Morrison, Jr. ............... | 128/303 |
| 4,312,337 A | 1/1982 | Donohue et al. | |
| 4,353,371 A | 10/1982 | Cosman ....................... | 128/303 |
| 4,492,231 A | 1/1985 | Auth ........................... | 128/303 |
| 4,590,934 A | 5/1986 | Malis et al. .................. | 128/303 |
| 4,628,943 A | 12/1986 | Miller | |
| 4,706,667 A | 11/1987 | Roos ........................... | 128/303 |

(Continued)

FOREIGN PATENT DOCUMENTS

DE  43 13 903 C1  9/1994

(Continued)

OTHER PUBLICATIONS

English abstract re Japanese Patent Application No. JP 1996000275351, published Apr. 28, 1997.

(Continued)

*Primary Examiner*—Lee S Cohen
(74) *Attorney, Agent, or Firm*—Cook Alex Ltd.

(57) ABSTRACT

A method and apparatus for creating transmural ablations in heart tissue, for example, may include two or more electrodes adapted to be connected to opposite poles of a bipolar RF generator so as to energize the electrodes to ablate cardiac tissue between the electrodes. A first electrode may be inserted into cardiac tissue at a first location and a second electrode may be inserted into cardiac tissue at a second location which is spaced from the first location. At least one of the electrodes may be adapted to provide a sufficiently low current density in the vicinity of the electrode to avoid substantial tissue desiccation when energized. Alternatively, the apparatus may include at least one bipolar ablation electrode which comprises an elongated conductive member of spiral shape having a pitch sufficiently small to provide sufficient surface area to avoid substantial desiccation of tissue when energized by a bipolar RF generator.

7 Claims, 3 Drawing Sheets

U.S. PATENT DOCUMENTS

| | | | |
|---|---|---|---|
| 4,732,149 A | 3/1988 | Sutter | 128/303 |
| 4,802,475 A | 2/1989 | Weshahy | 128/303 |
| 4,940,064 A | 7/1990 | Desai | 128/784 |
| 4,991,578 A | 2/1991 | Cohen | 128/419 |
| 5,009,661 A | 4/1991 | Michelson | |
| 5,013,312 A | 5/1991 | Parins et al. | 606/37 |
| 5,033,477 A | 7/1991 | Chin et al. | |
| 5,044,947 A | 9/1991 | Sachdeva et al. | |
| 5,071,428 A | 12/1991 | Chin et al. | |
| 5,083,565 A | 1/1992 | Parins | 128/642 |
| 5,085,657 A | 2/1992 | Ben-Simhon | 606/42 |
| 5,087,243 A | 2/1992 | Avitall | 604/20 |
| 5,116,332 A | 5/1992 | Lottick | 606/42 |
| 5,125,928 A | 6/1992 | Parins et al. | |
| 5,147,355 A | 9/1992 | Friedman | 606/23 |
| 5,190,541 A | 3/1993 | Abele et al. | 606/46 |
| 5,207,691 A | 5/1993 | Nardella | 606/142 |
| 5,217,460 A | 6/1993 | Knopfler | 606/52 |
| 5,231,995 A | 8/1993 | Desai | 128/784 |
| 5,242,441 A | 9/1993 | Avitall | 606/41 |
| 5,242,458 A | 9/1993 | Bendel et al. | |
| 5,250,047 A | 10/1993 | Rydell | 606/48 |
| 5,250,075 A | 10/1993 | Badie | 606/207 |
| 5,254,130 A | 10/1993 | Poncet et al. | |
| 5,263,493 A | 11/1993 | Avitall | 607/122 |
| 5,269,326 A | 12/1993 | Verrier | 128/642 |
| 5,269,780 A | 12/1993 | Roos | 606/42 |
| 5,281,215 A | 1/1994 | Milder | 606/20 |
| 5,281,216 A | 1/1994 | Klicek | 606/42 |
| 5,293,869 A | 3/1994 | Edwards et al. | 128/642 |
| 5,306,234 A | 4/1994 | Johnson | |
| 5,318,589 A | 6/1994 | Lichtman | 606/205 |
| 5,323,781 A | 6/1994 | Ideker et al. | |
| 5,327,905 A | 7/1994 | Avitall | 128/772 |
| 5,354,297 A | 10/1994 | Avitall | 606/45 |
| 5,357,956 A | 10/1994 | Nardella | 128/642 |
| 5,397,339 A | 3/1995 | Desai | 607/116 |
| 5,403,312 A | 4/1995 | Yates et al. | 606/50 |
| 5,423,807 A | 6/1995 | Milder | 606/20 |
| 5,429,131 A | 7/1995 | Scheinman et al. | 128/642 |
| 5,429,636 A | 7/1995 | Shikhman et al. | 606/41 |
| 5,438,302 A | 8/1995 | Goble | 331/167 |
| 5,441,483 A | 8/1995 | Avitall | 604/95 |
| 5,443,463 A | 8/1995 | Stern et al. | 606/51 |
| 5,445,638 A | 8/1995 | Rydell et al. | 606/51 |
| 5,449,355 A | 9/1995 | Rhum et al. | 606/41 |
| 5,451,223 A | 9/1995 | Ben-Simhon | 606/42 |
| 5,452,733 A | 9/1995 | Sterman et al. | |
| 5,454,370 A | 10/1995 | Avitall | 128/642 |
| 5,465,716 A | 11/1995 | Avitall | 128/642 |
| 5,472,441 A | 12/1995 | Edwards et al. | 606/41 |
| 5,478,309 A | 12/1995 | Sweezer et al. | 604/4 |
| 5,480,409 A | 1/1996 | Riza | 606/205 |
| 5,487,385 A | 1/1996 | Avitall | 128/642 |
| 5,496,312 A | 3/1996 | Klicek | 606/34 |
| 5,500,011 A | 3/1996 | Desai | 607/116 |
| 5,500,012 A | 3/1996 | Brucker et al. | |
| 5,531,744 A | 7/1996 | Nardella et al. | 606/48 |
| 5,536,267 A | 7/1996 | Edwards et al. | 606/41 |
| 5,549,636 A | 8/1996 | Li | |
| 5,555,883 A | 9/1996 | Avitall | 128/642 |
| 5,562,699 A | 10/1996 | Heimberger et al. | |
| 5,562,700 A | 10/1996 | Huitema et al. | |
| 5,562,721 A | 10/1996 | Marchlinski et al. | 607/99 |
| 5,564,440 A | 10/1996 | Swartz et al. | 128/898 |
| 5,571,215 A | 11/1996 | Sterman et al. | |
| 5,575,766 A | 11/1996 | Swartz et al. | |
| 5,575,805 A | 11/1996 | Li | |
| 5,582,609 A | 12/1996 | Swanson et al. | 606/39 |
| 5,587,723 A | 12/1996 | Otake et al. | 345/118 |
| 5,595,183 A | 1/1997 | Swanson et al. | 128/697 |
| 5,599,350 A | 2/1997 | Schulze et al. | 606/51 |
| 5,611,813 A | 3/1997 | Lichtman | 606/205 |
| 5,620,459 A | 4/1997 | Lichtman | 606/205 |
| 5,642,736 A | 7/1997 | Avitall | 128/772 |
| 5,655,219 A | 8/1997 | Jusa et al. | 370/338 |
| 5,672,174 A | 9/1997 | Gough et al. | 606/41 |
| 5,674,220 A | 10/1997 | Fox et al. | 606/51 |
| 5,680,860 A * | 10/1997 | Imran | 600/374 |
| 5,683,384 A | 11/1997 | Gough et al. | 606/41 |
| 5,687,737 A | 11/1997 | Branham et al. | 128/710 |
| 5,688,270 A | 11/1997 | Yates et al. | 606/51 |
| 5,690,611 A | 11/1997 | Swartz et al. | 604/53 |
| 5,693,051 A | 12/1997 | Schulze et al. | 606/51 |
| 5,697,925 A | 12/1997 | Taylor | 606/34 |
| 5,697,928 A | 12/1997 | Walcott et al. | 606/41 |
| 5,702,359 A | 12/1997 | Hofmann et al. | 604/20 |
| 5,702,390 A | 12/1997 | Austin et al. | 606/48 |
| 5,702,438 A | 12/1997 | Avitall | 607/122 |
| 5,709,680 A | 1/1998 | Yates et al. | 606/50 |
| 5,718,703 A | 2/1998 | Chin | 606/49 |
| 5,722,403 A | 3/1998 | McGee et al. | 128/642 |
| 5,725,512 A | 3/1998 | Swartz et al. | 604/280 |
| 5,728,143 A | 3/1998 | Gough et al. | 607/101 |
| 5,730,127 A | 3/1998 | Avitall | 128/642 |
| 5,730,704 A | 3/1998 | Avitall | 600/374 |
| 5,733,280 A | 3/1998 | Avitall | 606/23 |
| 5,735,847 A | 4/1998 | Gough et al. | 606/45 |
| 5,735,849 A | 4/1998 | Baden et al. | 606/51 |
| 5,740,808 A | 4/1998 | Panescu et al. | 128/662 |
| 5,755,664 A | 5/1998 | Rubenstein | 600/377 |
| 5,755,717 A | 5/1998 | Yates et al. | 606/51 |
| 5,759,158 A | 6/1998 | Swanson | 600/508 |
| 5,776,130 A | 7/1998 | Buysse et al. | |
| 5,782,827 A | 7/1998 | Gough et al. | 606/41 |
| 5,782,828 A | 7/1998 | Chen et al. | 606/42 |
| 5,785,706 A | 7/1998 | Bednarek | 606/41 |
| H1745 H | 8/1998 | Paraschac | 606/51 |
| 5,797,906 A | 8/1998 | Rhum et al. | 606/48 |
| 5,797,960 A | 8/1998 | Stevens et al. | 606/213 |
| 5,800,484 A | 9/1998 | Gough et al. | 607/104 |
| 5,807,393 A | 9/1998 | Williamson, IV et al. | 606/32 |
| 5,807,395 A | 9/1998 | Mulier et al. | 606/41 |
| 5,810,804 A | 9/1998 | Gough et al. | 606/41 |
| 5,810,805 A | 9/1998 | Sutcu et al. | 606/45 |
| 5,810,811 A | 9/1998 | Yates et al. | 606/50 |
| 5,814,028 A | 9/1998 | Swartz et al. | |
| 5,817,091 A | 10/1998 | Nardella et al. | 606/38 |
| 5,823,955 A | 10/1998 | Kuck et al. | 600/374 |
| 5,823,956 A | 10/1998 | Roth et al. | 600/374 |
| 5,829,447 A | 11/1998 | Stevens et al. | 128/898 |
| 5,833,690 A | 11/1998 | Yates et al. | 606/52 |
| 5,833,703 A | 11/1998 | Manushakian | 606/174 |
| 5,842,984 A | 12/1998 | Avitall | 600/374 |
| 5,843,075 A | 12/1998 | Taylor | 606/34 |
| 5,843,122 A | 12/1998 | Riza | 606/207 |
| 5,846,238 A | 12/1998 | Jackson et al. | 606/41 |
| 5,849,011 A | 12/1998 | Jones et al. | 606/47 |
| 5,849,020 A | 12/1998 | Long et al. | 606/167 |
| 5,853,411 A | 12/1998 | Whayne et al. | 606/41 |
| 5,855,590 A | 1/1999 | Malecki et al. | |
| 5,855,614 A | 1/1999 | Stevens et al. | 623/11 |
| 5,860,975 A | 1/1999 | Goble et al. | 606/45 |
| 5,863,290 A | 1/1999 | Gough et al. | 606/41 |
| 5,863,291 A | 1/1999 | Schaer | 606/41 |
| 5,868,737 A | 2/1999 | Taylor et al. | 606/34 |
| 5,871,483 A | 2/1999 | Jackson et al. | 606/41 |
| 5,873,896 A | 2/1999 | Ideker | 607/14 |
| 5,876,398 A | 3/1999 | Mulier et al. | |
| 5,876,400 A | 3/1999 | Songer | 606/45 |
| 5,876,401 A | 3/1999 | Schulze et al. | 606/51 |
| 5,891,135 A | 4/1999 | Jackson et al. | 606/41 |
| 5,891,136 A | 4/1999 | McGee et al. | 606/41 |
| 5,891,138 A | 4/1999 | Tu et al. | |

| | | | |
|---|---|---|---|
| 5,893,863 A | 4/1999 | Yoon | 606/170 |
| 5,893,885 A * | 4/1999 | Webster, Jr. | 607/122 |
| 5,897,554 A | 4/1999 | Chia et al. | |
| 5,899,898 A | 5/1999 | Arless et al. | 606/22 |
| 5,899,899 A | 5/1999 | Arless et al. | 606/22 |
| 5,902,289 A | 5/1999 | Swartz et al. | 604/281 |
| 5,910,129 A | 6/1999 | Koblish et al. | 604/95 |
| 5,913,855 A | 6/1999 | Gough et al. | 606/41 |
| 5,921,924 A | 7/1999 | Avitall | 600/374 |
| 5,921,982 A | 7/1999 | Lesh et al. | |
| 5,924,424 A | 7/1999 | Stevens et al. | 128/898 |
| 5,925,038 A | 7/1999 | Panescu et al. | 606/41 |
| 5,925,042 A | 7/1999 | Gough et al. | 606/41 |
| 5,928,229 A | 7/1999 | Gough et al. | 606/41 |
| 5,931,836 A | 8/1999 | Hatta et al. | 606/38 |
| 5,935,123 A | 8/1999 | Edwards et al. | |
| 5,935,126 A | 8/1999 | Riza | 606/51 |
| 5,938,660 A | 8/1999 | Swartz et al. | 606/45 |
| 5,941,251 A | 8/1999 | Panescu et al. | 128/899 |
| 5,941,845 A | 8/1999 | Tu et al. | 604/53 |
| 5,944,718 A | 8/1999 | Austin et al. | 606/48 |
| 5,947,938 A | 9/1999 | Swartz et al. | 604/280 |
| 5,951,547 A | 9/1999 | Gough et al. | 606/41 |
| 5,951,552 A | 9/1999 | Long et al. | 606/46 |
| 5,954,665 A | 9/1999 | Ben-Haim | 600/515 |
| 5,961,514 A | 10/1999 | Long et al. | 606/41 |
| 5,967,976 A | 10/1999 | Larsen | 600/374 |
| 5,971,983 A | 10/1999 | Lesh | 606/41 |
| 5,972,026 A | 10/1999 | Laufer et al. | 607/96 |
| 5,980,516 A | 11/1999 | Mulier et al. | 606/41 |
| 5,980,517 A | 11/1999 | Gough | 606/41 |
| 5,984,281 A | 11/1999 | Hacker et al. | 261/71 |
| 5,997,533 A | 12/1999 | Kuhns | 606/41 |
| 6,010,516 A | 1/2000 | Hulka | 606/148 |
| 6,010,531 A | 1/2000 | Donlon et al. | 623/2 |
| 6,012,457 A | 1/2000 | Lesh | 128/898 |
| 6,013,074 A | 1/2000 | Taylor | 606/34 |
| 6,016,809 A | 1/2000 | Mulier et al. | 128/898 |
| 6,017,358 A | 1/2000 | Yoon et al. | 606/205 |
| 6,023,638 A | 2/2000 | Swanson | 600/510 |
| 6,024,740 A | 2/2000 | Lesh et al. | 606/34 |
| 6,024,741 A | 2/2000 | Williamson, IV et al. | 606/40 |
| 6,030,403 A | 2/2000 | Long et al. | 606/185 |
| 6,033,402 A | 3/2000 | Tu et al. | |
| 6,036,670 A | 3/2000 | Wijeratne et al. | 604/96 |
| 6,039,731 A | 3/2000 | Taylor et al. | 606/34 |
| 6,039,733 A | 3/2000 | Buyssee et al. | 606/40 |
| 6,039,748 A | 3/2000 | Savage et al. | 606/180 |
| 6,047,218 A | 4/2000 | Whayne et al. | 607/122 |
| 6,048,329 A | 4/2000 | Thompson et al. | 604/95 |
| 6,050,996 A | 4/2000 | Schmaltz et al. | |
| 6,064,902 A | 5/2000 | Haissaguerre et al. | |
| 6,068,653 A | 5/2000 | LaFontaine | |
| 6,071,281 A | 6/2000 | Burnside et al. | |
| 6,083,150 A | 7/2000 | Aznoian et al. | |
| 6,083,222 A | 7/2000 | Klien et al. | |
| 6,096,037 A | 8/2000 | Mulier et al. | |
| 6,110,098 A | 8/2000 | Renirie et al. | 600/16 |
| 6,113,595 A | 9/2000 | Muntermann | |
| 6,113,598 A | 9/2000 | Baker | |
| 6,117,101 A | 9/2000 | Diederich et al. | |
| 6,123,703 A | 9/2000 | Tu et al. | |
| 6,126,658 A | 10/2000 | Baker | |
| 6,142,994 A | 11/2000 | Swanson et al. | |
| 6,156,033 A | 12/2000 | Tu et al. | |
| 6,161,543 A | 12/2000 | Cox et al. | |
| 6,162,220 A | 12/2000 | Nezhat | 606/48 |
| 6,193,713 B1 | 2/2001 | Geistert et al. | |
| 6,237,605 B1 | 5/2001 | Vaska et al. | |
| 6,264,087 B1 | 7/2001 | Whitman | |
| 6,267,761 B1 | 7/2001 | Ryan | |
| 6,273,887 B1 | 8/2001 | Yamauchi et al. | |
| 6,277,117 B1 | 8/2001 | Tetzlaff et al. | |
| 6,292,678 B1 | 9/2001 | Hall et al. | |
| 6,296,640 B1 | 10/2001 | Wampler et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,332,089 B1 | 12/2001 | Acker et al. | |
| 6,334,860 B1 | 1/2002 | Dorn | |
| 6,356,790 B1 | 3/2002 | Maguire et al. | |
| 6,358,249 B1 | 3/2002 | Chen et al. | |
| 6,391,024 B1 | 5/2002 | Sun et al. | |
| 6,443,970 B1 | 9/2002 | Schulze et al. | |
| 6,447,507 B1 | 9/2002 | Bednarek et al. | |
| 6,464,700 B1 | 10/2002 | Koblish et al. | |
| 6,474,340 B1 | 11/2002 | Vaska et al. | |
| 6,488,678 B2 | 12/2002 | Sherman | |
| 6,488,680 B1 | 12/2002 | Francischelli et al. | |
| 6,491,689 B1 | 12/2002 | Ellis et al. | |
| 6,497,704 B2 | 12/2002 | Ein-Gal | |
| 6,506,189 B1 | 1/2003 | Rittman, III et al. | |
| 6,517,536 B2 * | 2/2003 | Hooven et al. | 606/41 |
| 6,540,740 B2 | 4/2003 | Lehmann et al. | |
| 6,546,935 B2 | 4/2003 | Hooven | |
| 6,575,969 B1 | 6/2003 | Rittman, III et al. | |
| 6,610,055 B1 | 8/2003 | Swanson et al. | |
| 6,632,222 B1 | 10/2003 | Edwards et al. | |
| 6,669,691 B1 | 12/2003 | Taimisto | |
| 6,679,882 B1 | 1/2004 | Kornerup | |
| 6,692,491 B1 | 2/2004 | Phan | |
| 7,120,504 B2 | 10/2006 | Osypka | |
| 2001/0031961 A1 | 10/2001 | Hooven | |
| 2001/0039419 A1 | 11/2001 | Francischelli et al. | |
| 2002/0002329 A1 | 1/2002 | Avitall | |
| 2002/0019629 A1 | 2/2002 | Dietz et al. | |
| 2002/0032440 A1 | 3/2002 | Hooven | |
| 2002/0052602 A1 | 5/2002 | Wang et al. | |
| 2002/0082595 A1 | 6/2002 | Langberg et al. | |
| 2002/0091382 A1 | 7/2002 | Hooven | |
| 2002/0091383 A1 | 7/2002 | Hooven | |
| 2002/0091384 A1 | 7/2002 | Hooven | |
| 2002/0099364 A1 | 7/2002 | Lalonde | |
| 2002/0103484 A1 | 8/2002 | Hooven | |
| 2002/0107513 A1 | 8/2002 | Hooven | |
| 2002/0107514 A1 | 8/2002 | Hooven | |
| 2002/0111618 A1 * | 8/2002 | Stewart et al. | 606/41 |
| 2002/0115990 A1 | 8/2002 | Acker | |
| 2002/0115993 A1 | 8/2002 | Hooven | |
| 2002/0120263 A1 | 8/2002 | Brown et al. | |
| 2002/0120316 A1 | 8/2002 | Hooven | |
| 2002/0128643 A1 | 9/2002 | Simpson et al. | |
| 2002/0183738 A1 | 12/2002 | Chee et al. | |
| 2003/0004507 A1 | 1/2003 | Francischelli et al. | |
| 2003/0009094 A1 | 1/2003 | Segner et al. | |
| 2003/0018329 A1 | 1/2003 | Hooven | |
| 2003/0028187 A1 | 2/2003 | Vaska et al. | |
| 2003/0045871 A1 | 3/2003 | Jain et al. | |
| 2003/0050557 A1 | 3/2003 | Susil et al. | |
| 2003/0060822 A1 | 3/2003 | Schaer et al. | |
| 2003/0069572 A1 | 4/2003 | Wellman et al. | |
| 2003/0069577 A1 | 4/2003 | Vaska et al. | |
| 2003/0073991 A1 | 4/2003 | Francischelli et al. | |
| 2003/0078570 A1 | 4/2003 | Heiner et al. | |
| 2003/0078574 A1 | 4/2003 | Hall et al. | |
| 2003/0093068 A1 | 5/2003 | Hooven | |
| 2003/0093104 A1 | 5/2003 | Bonner et al. | |
| 2003/0097124 A1 | 5/2003 | Lehmann et al. | |
| 2003/0100895 A1 | 5/2003 | Simpson et al. | |
| 2003/0114844 A1 | 6/2003 | Ormsby et al. | |
| 2003/0120268 A1 | 6/2003 | Bertolero et al. | |
| 2003/0125726 A1 | 7/2003 | Maguire et al. | |
| 2003/0125729 A1 | 7/2003 | Hooven | |
| 2003/0125730 A1 | 7/2003 | Berube et al. | |
| 2003/0130598 A1 | 7/2003 | Manning et al. | |
| 2003/0135207 A1 | 7/2003 | Langberg et al. | |

| | | | |
|---|---|---|---|
| 2003/0144657 | A1 | 7/2003 | Bowe et al. |
| 2003/0158548 | A1 | 8/2003 | Phan et al. |
| 2003/0171745 | A1 | 9/2003 | Francischelli et al. |
| 2003/0178032 | A1 | 9/2003 | Ingle et al. |

FOREIGN PATENT DOCUMENTS

| | | | |
|---|---|---|---|
| EP | 0 450 608 | A1 | 10/1991 |
| EP | 0 765 639 | | 4/1997 |
| WO | WO 92/05828 | A1 | 4/1992 |
| WO | WO 93/25267 | A1 | 12/1993 |
| WO | WO 97/10764 | A1 | 3/1997 |
| WO | WO 97/32525 | | 9/1997 |
| WO | WO 98/17187 | | 4/1998 |
| WO | WO 98/53750 | | 12/1998 |
| WO | WO 99/02096 | | 1/1999 |
| WO | WO 99/04696 | | 2/1999 |
| WO | WO 99/12487 | | 3/1999 |
| WO | WO 99/44519 | | 9/1999 |
| WO | WO 99/56486 | A2 | 11/1999 |
| WO | WO 99/56486 | A3 | 11/1999 |
| WO | WO 99/56644 | | 11/1999 |
| WO | WO 99/56648 | | 11/1999 |
| WO | WO 99/59486 | | 11/1999 |
| WO | WO 00/21449 | | 4/2000 |
| WO | WO 00/27310 | A2 | 5/2000 |
| WO | WO 00/27310 | A3 | 5/2000 |
| WO | WO 00/27311 | | 5/2000 |
| WO | WO 00/27312 | | 5/2000 |
| WO | WO 00/27313 | | 5/2000 |
| WO | WO 00/42931 | | 7/2000 |
| WO | WO 00/42932 | | 7/2000 |
| WO | WO 00/42933 | | 7/2000 |
| WO | WO 00/42934 | | 7/2000 |
| WO | WO 01/82812 | A1 | 11/2001 |
| WO | WO 01/82813 | A2 | 11/2001 |
| WO | WO 01/82813 | A3 | 11/2001 |
| WO | WO 02 / 087454 | A1 | 11/2002 |

OTHER PUBLICATIONS

Yoshio Kosakai, M.D., et al., "Cox Maze Procedure for Chronic Atrial Fibrillation Associated with Mitral Valve Disease," The Journal of Thoracic and Cardiovascular Surgery, 1994; vol. 108, No. 6, pp. 1049-1055.

Ki-Bong Kim, M.D., et al., Abstract "The Cox-Maze III Procedure for Atrial Fibrillation Associated with Rheumatic Mitral Valve Disease," The Annals of Thoracic Surgery, 2000; pp. 1-5.

Hiroshi Nakagawa, et al., Abstract, "Creation of Long Linear Transmural Radiofrequency Lesions in Atrium Using a Novel Spiral Ribbon—Saline Irrigated Electrode Catheter," Journal of American College of Cardiology, Feb. 1996.

Taijiro Sueda, et al., "Efficacy of a Simple Left Atrial Procedure for Chronic Atrial Procedure for Chronic Atrial Fibrillation in Mitral Valve Operations," The Annals of Thoracic Surgery, 1997, vol. 63, pp. 1070-1073.

Mien-Cheng Chen, M.D., et al., "Radiofrequency and Cryoablation of Atrial Fibrillation in Patients Undergoing Valvular Operations," Anals of Thoracic Surgery, 1998:65:1666-1672.

Arif Elvan, M.D., et al., Abstract, "Radiofrequency Catheter Ablation of the Atria Reduces Inducibility and Duration of Atrial Fibrillation in Dogs," Circulation, 1995:91:2235-2244.

Warren M. Jackman, M.D., et al.., "Radiofrequency Current Directed Across the Mitral Anulus With a Bipolar Epicardial-Endocardial Catheter Electrode Configuration in Dogs," Circulation, 1988; vol. 78, No. 5, pp. 1288-1297.

James L. Cox, M.D., Ed., "Seminars in Thoracic and Cardiovascular Surgery: The Maze Procedure for Atrial Fibrillation," 2000, vol. 12, No. 1.

Lauran Neergaard, "Slicing a Heart to Make It Beat," Article from The Associated Press, Mar. 26, 1998 Website (www.nando.com/newsroom/ntn/health/032698/health24_22737_body.html).

Yoshito Inoue, et al., "Video Assisted Thoracoscopic and Cardioscopic Radiofrequency Maze Ablation," Asaio Journal, 1997, pp. 334-337.

Yoshito Inoue, et al., Abstract, "Video Assisted Thoracoscopic and Cardioscopic Radiofrequency Maze Ablation," Asaio Journal, 1997.

Mary O. Palazzo, RN, MS, CCRN, "What You Need To Know—a-fib 101," from the Atrial Fibrillation Page Website (www.members.aol.com/mazern/afib101.htm) Jun. 5, 2000.

Mary O. Palazzo, RN, MS, CCRN, "What You Need To Know—maze FAQ," from the Atrial Fibrillation Page Website (www.members.aol.com/mazern/mazefaq.htm) Nov. 25, 1999.

Mary O. Palazzo, RN, MS, CCRN, "What You Need To Know—maze FAQ," from the Atrial Fibrillation Page Website (www.members.aol.com/mazern/mazefaq.htm) Jun. 21, 2000.

Ivan M. Robbins, M.D., et al., "Pulmonary Vein Stenosis After Catheter Ablation of Atrial Fibrillation," Circulation, 1998; 98:1769-1775.

Akira t. Kawaguchi, et al., "Factors Affecting Rhythm After the Maze Procedure for Atrial Fibrillation," Circulation, 1998; vol. 78, No. 5, pp. 1288-1296.

Taijiro Sueda, et al., "Simple Left Atrial Procedure for Chronic Atrial Fibrillation Associated with Mitral Valve Disease," The Annals of Thoracic Surgery, 1996;62:1796-1800.

Berjano, Enrique J. et al. "Bipolar Electrosurgery With Long Electrodes for RF Coagulation of Atrial Tissue" Proceedings 19th International Conference—IEEE/EMBS Oct. 30-Nov. 2, 1997 Chicago, Il. USA. pp. 2528-2530.

PCT International Search Report dated Sep. 22, 2006, 2 pages.

Written Opinion of the International Searching Authority dated Sep. 22, 2006, 3 pages.

* cited by examiner

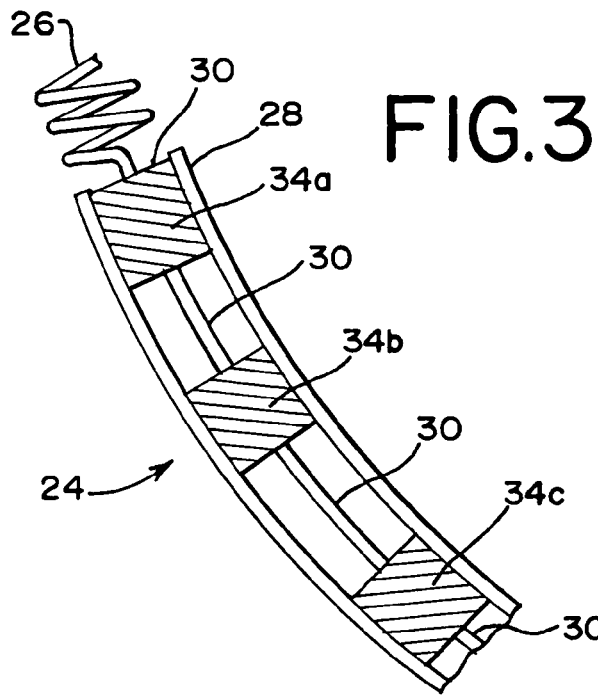
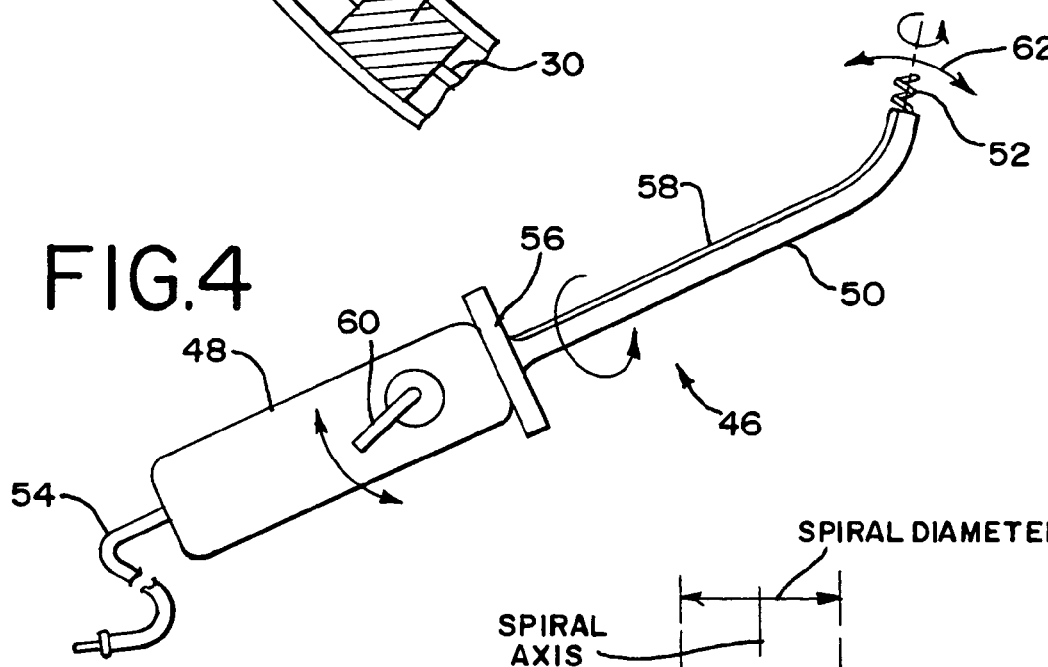
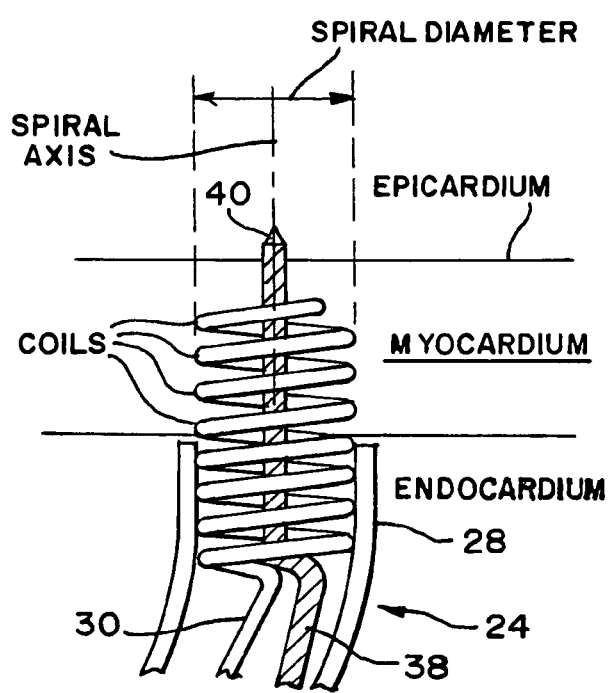

BIPOLAR TRANSMURAL ABLATION METHOD AND APPARATUS

CROSS REFERENCE TO RELATED APPLICATION

This application is a non-provisional application which claims the benefit of provisional application Ser. No. 60/561,937, filed Apr. 14, 2004, which application is incorporated by reference herein.

BACKGROUND OF THE INVENTION

Atrial fibrillation is one of the most common heart arrhythmias in the world, affecting over 2.5 million people in the United States alone. Ablation of cardiac tissue to create scar tissue that interrupts the path of the errant electrical impulses in the heart tissue is one method for treating cardiac arrhythmia. Such ablation may take the form of one or more lines or points of ablation of heart tissue, to a series of ablations that form a strategic placement of ablation lines in, around or in proximity to one or both atria to stop the conduction and/or formation of errant impulses.

More particularly, the pattern of ablation lines may be similar to the pattern of surgical lines that are created in the so-called "Maze" procedure, which was first developed as an open chest procedure. To reduce the trauma associated with the Maze surgical procedure, substantial efforts have been made to achieve similar results via less invasive ablation techniques. Among other things, the Maze procedure includes a series of transmural ablations or lesions to be formed on the atrium in the vicinity of the pulmonary veins. A series of lesions that may be made during the Maze procedure are shown in various prior patents or articles such as U.S. Pat. Nos. 6,517,536 and 6,546,935, both to Hooven and assigned to AtriCure, Inc.

SUMMARY OF THE INVENTION

The present invention relates to systems, methods and apparatuses for creating transmural ablations in heart tissue. In general terms, the apparatus may include two or more electrodes adapted to be connected to a bipolar electrosurgical RF generator so as to be of the opposite polarity. In accordance with one aspect of the present invention, the electrode or the distal end of the electrode is preferably fashioned to provide a large electrode surface area to provide relatively low current density in the vicinity of the electrode, thereby reducing the tissue desiccation and resultant high resistance that can occur in proximity to the electrode with prior art electrodes of linear or high-pitch threaded designs.

An electrode embodying the present invention may take different forms, but in one preferred embodiment, the electrode comprises a relatively low-pitch helical or coil configuration of electrically conductive material that is adapted to be threaded or screwed into the myocardium of the heart. Each such electrode may optionally include at its distal end a mass or slug (also called a "sink") of material of a highly electrically and thermally conductive material that contacts the endocardium, such as in proximity to the electrode, when the electrode is screwed into the myocardium. For purposes of this application, the term "low-pitch" electrode is intended to refer generally to an electrode that provides a relatively large surface area within the heart tissue as compared to a linear or high pitch electrode and includes, without limitation, a helical, spiral coil, screw or other shape, type or style of electrode. For purposes of this description, "spiral" is intended to include spiral, helical, coil and screw shapes, not limited to "hollow" spiral devices and "coil" and "screw" are used interchangeably and generically.

In use, each electrode is inserted, such as by screw action or the like depending on the electrode shape, into the heart tissue, with care being taken to ensure that the conductive coil preferably does not completely puncture the heart wall (although the present invention is not limited to a non-puncture application). The second electrode is similarly inserted into the heart tissue at a location spaced a selected distance, such as from about 1 to 4 cm from the first electrode. When attached to the RF generator, one electrode is positively charged and the other is negatively charged. When the generator is activated, bipolar RF energy flows between the electrodes through the tissue, forming a transmural (through the heart wall) ablation line extending through the thickness of the heart tissue and between the electrodes. One of the electrodes may then be withdrawn and inserted into the cardiac tissue at a selected distance from the other electrode to form another or second segment of an ablation line. After the second segment is formed, the other electrode may be removed and reinserted at a location spaced from the one electrode to form a third ablation line segment. This procedure may be repeated as needed to form the desired ablation line.

The present invention may be performed epicardially by inserting the electrodes from the outside surface of the heart tissue or endocardially by inserting the electrode from inside the heart, where they may be advanced by a catheter or other instrument. Either way, the present invention lends itself to a minimally invasive procedure for forming ablation lines with comparative little trauma as compared to a Maze surgical procedure.

The low-pitch electrodes of the present invention use a highly thermally conductive material and present a relatively large amount of surface area that is in contact with the tissue to be ablated. The large surface area in the illustrated embodiment is due to the low pitch coil, and may be enhanced by the use of the mass or slug mentioned earlier. Because the electrode/tissue contact area is large, and preferably maximized, the current density at the electrode/tissue interface is relatively low and, preferably, minimized. Complemented by the mass or slug structure, which serves to remove heat from the tissue surrounding the electrode, undue tissue coagulation is reduced at or near the electrode. Additionally, coagulation remote from the electrodes, that is in the line between the two electrodes, is relatively increased.

In accordance with another aspect of the present invention, each electrode includes an EKG probe wire or sensor that extends distally from the electrode just beyond the termination of the conductive electrode. The distal-most tip of the EKG wire or sensor is exposed so that as the coil electrode is inserted into the heart tissue, the EKG wire is simultaneously advanced. The EKG wire exits the inner or outer surface of the myocardial tissue (depending on the direction of insertion) just before the coil electrode penetrates through the entire tissue thickness. The cardiologist or electrophysiologist can determine when the exposed tip of the EKG wire exits the myocardium by viewing the EKG signal generated by the tip of the wire. As long as the tip of the wire is within the myocardial tissue, an EKG signal is generated. When the tip exits the tissue, the EKG decreases or disappears abruptly. The cardiologist then knows that the coil of the electrode is properly positioned in the tissue, so that it extends essentially entirely through the tissue thickness without completely puncturing the wall. Alternatively, the sensor may be located on the end of the EKG electrode so that advancement of the electrode through the cardiac tissue is immediately detected with the distal end of the electrode exits the tissue. The EKG sensor may also aid the surgeon in determining the proper placement of the electrode in the heart tissue.

BRIEF DESCRIPTION OF THE DRAWINGS

FIG. 3 is an enlarged cross-sectional view of a first alternate embodiment of an electrode embodying a plurality of slugs or sinks.

FIG. 4 is a plan view of an electrode according to the present invention including a hand-piece.

FIG. 5 is an enlarged cross-sectional view of the distal end of a second alternate embodiment of an electrode employing an EKG sensor according to the present invention showing the electrode attached to heart tissue.

DETAILED DESCRIPTION

Figure 1:
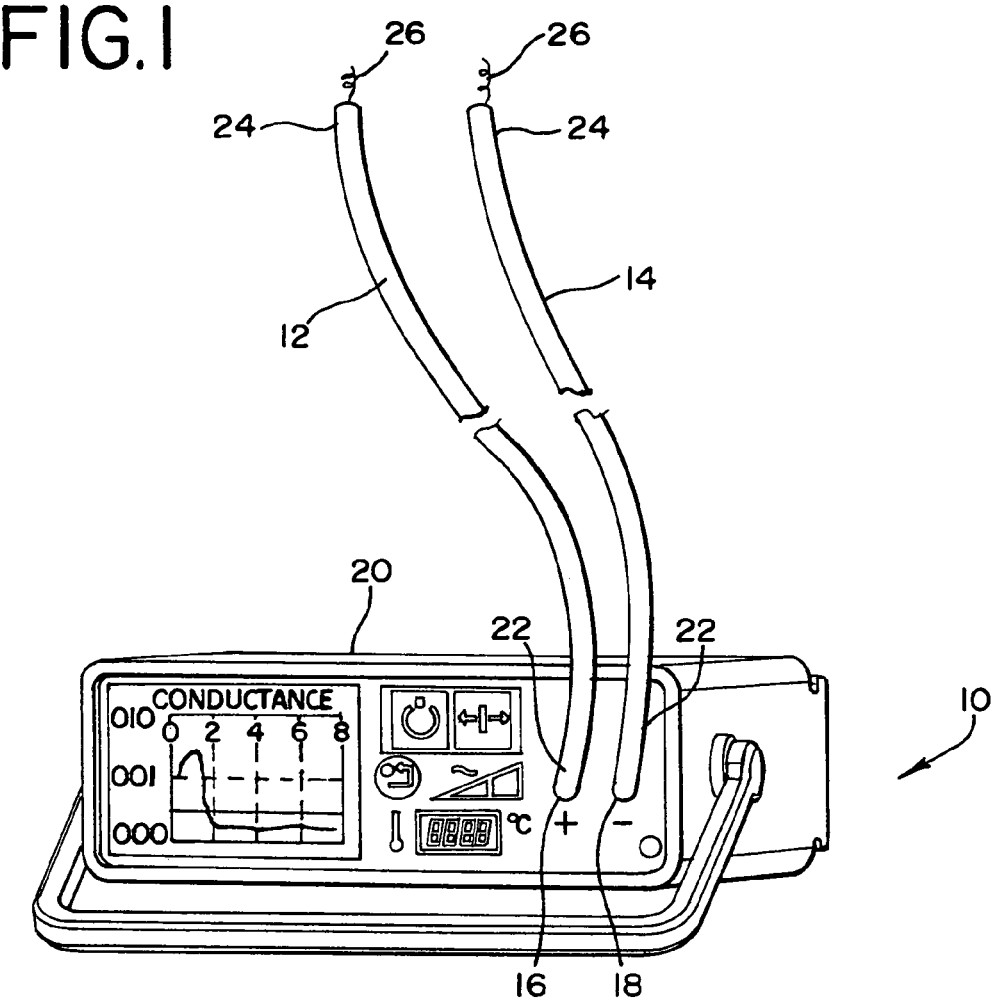
FIG. 1 is a perspective view of a system employing bipolar ablation electrodes according to the present invention, and more particularly low-pitch spiral or screw-shaped electrodes.

Turning to the figures of the drawings, there is seen in FIG. 1 an electrosurgical system, generally designated 10, embodying the present invention. System 10 comprises a pair of substantially identical electrodes, or electrode leads generally at 12, 14, each of which is adapted to be connected to one of the positive terminal 16 or negative terminal 18 of an electrosurgical bipolar RF generator 20. The connections between the electrodes and the generator, as well as the structure of the generator itself, are well known and are not described in detail herein. Although each electrode in FIG. 1 is preferably identical, such may not be required in accordance with broader aspects of the invention, and only one electrode embodying the present invention may be employed. There may be circumstances where electrode of different shape may be employed. Similarly, there may be circumstances where more than two electrodes are used simultaneously—for example one (or more) electrode may be connected to one terminal of the generator and two (or more) electrodes connected to the other terminal to form two or more ablation line segments at the same time.

Figure 2:
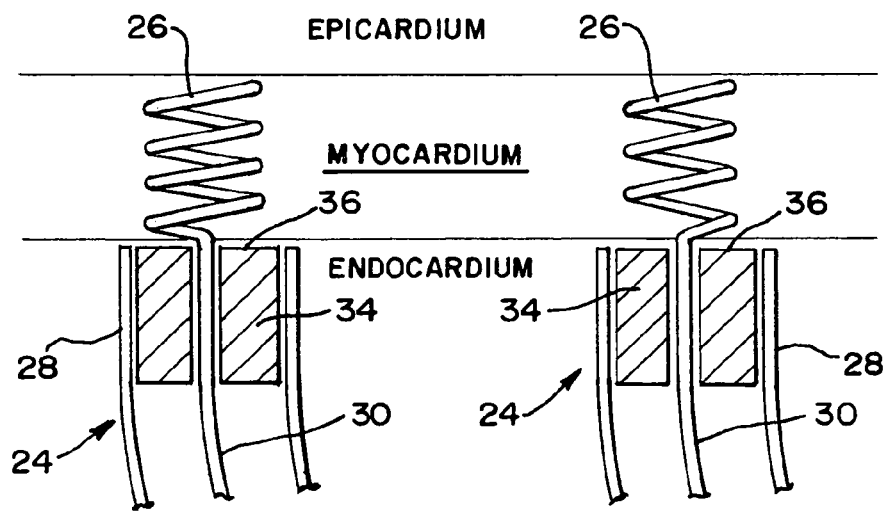
FIG. 2 is an enlarged cross-sectional view of the distal ends of a pair of electrodes embodying aspects of the present invention showing the electrodes attached to heart tissue.

Each illustrated electrode 12, 14 has a proximal end 22, which is adapted to be connected to one of the positive or negative terminals of the RF generator, and a distal end 24 that terminates in an electrode 26 that generates low current density and that is adapted to be inserted into tissue, such as that of the heart. With reference to FIG. 2, each electrode preferably comprises an outer tubular insulating member 28 that extends from the proximal end to the electrode 26 at the distal end. The insulating tube 28 is preferably made of a polymer such as PTFE, nylon or silicon and has an outside diameter of typically 1 mm to 4 mm, although the material and size may vary. A conductive member or wire 30 extends through the insulating tube 28 to conduct RF energy from the generator to the conductive terminal electrode 26. Alternatively, the elongated conductor may be referred to as a lead or wire and the terminal member 26 referred to as the electrode. The terminal end electrode 26 may be separable from the elongated lead or conductor for replacement as needed.

The conductive member 30 is preferably in the form of a separate copper wire, but may alternatively comprise a thin conductive film, or other conductive element or means that, for example, may extend along or within the wall of tube 28.

The low current density electrode 26 may comprise a low pitch, small diameter coil or spiral wire that is integral with or otherwise in electrical contact with the distal end of the conductive wire 30. The coil is also preferably made of solid copper, but may also be a plated copper, such as gold plated, stainless steel, or other conductive materials such as aluminum or beryllium-copper of sufficient strength to allow it to be threaded or screwed into the cardiac tissue. To this end, the tip of the electrode may be tapered to a point for piercing the myocardium.

The diameter of the wire comprising the coil or spiral is preferably about 0.01 inches (0.254 mm), but may range between about 0.005 inches (0.127 mm) and 0.025 inches (0.635 mm), while the diameter of the coil itself may be, for example, between about 0.080 inches (2 mm) and 0.20 inches (5 mm).

The pitch of the coil electrode is defined as the axial distance between adjacent coils of the wire. For purposes of clarity, it should be noted that, as the number of coils increases per unit of axial length, the pitch (or distance between adjacent coils) decreases. Conversely, as the number of coils decreases per unit of axial length, the pitch (or distance between adjacent coils) increases.

Low pitch for purposes of this description is preferably lower than about 3 coils per 5 mm, with the lower pitch spiral being preferred. The pitch of the thread of the conductive coil or screw is preferably about 1 coil (360° extent) per 1 mm of the axial extent of the coil or more, but may be about 2 coils per 1 mm. The small diameter of the wire and the low pitch tend to increase and maximize the contact area between the electrode with the tissue to which it is attached.

Low current density for purposes of this description is about 20 milliamperes per square millimeter (20 ma/mm$^2$) or less. By way of example, and not limitation, a current density of approximately 16.2 ma/mm$^2$ is provided by an electrode that has a wire diameter of 0.01 inches (0.254 mm), a pitch of about 1 coil/mm, a coil diameter of about 0.20 inches (5 mm), which electrode extends through approximately 0.20 inches (5 mm) of tissue (with about 5 coils located in the tissue) and with a current flow of about 1 ampere (1000 ma). Such an electrode has about 62 mm$^2$ of surface area in contact with the cardiac tissue.

The current density is calculated by dividing the current flow by the electrode surface area (or current density=current flow/electrode surface area). For a current flow of 1 ampere (1000 ma) and an electrode surface area of 62 mm$^2$, the current density is 1 ampere (1000 ma)/62 mm$^2$ or about 16.2 ma/mm$^2$. Other current densities are possible for other configurations of the electrode and also will depend on the number of electrodes employed. Typically, for electrodes located about 2 cm apart in cardiac tissue, a current flow of about 1 ampere is needed to create an ablation line therebetween.

In addition, the distal end of each electrode may include a slug 34 or a mass of material (or "sink") such as copper or a copper/aluminum alloy that surrounds the conductive wire 30. The distal end 36 of the slug 34 may be coterminus with, or extend slightly beyond, the distal end of the outer insulating member 28 so that when the electrode is screwed into tissue, the surface 36 of the slug 34 contacts the surface of the tissue. Thus, when the electrode is attached to the tissue, the slug or mass 34 optionally serves to even further increase the contact area of the electrode, and to provide a mass of material that acts as a heat sink to limit tissue temperature increases.

As seen in FIG. 3, the electrodes 12 and 14 may include a series of slugs or masses 34a, 34b, 34c at the distal end 24 connected in series to the conductive wire 30 to provide for a higher rate of thermal dissipation. As illustrated, the masses or slugs 34a, 34b, 34c are spaced along the wire 30 to provide for flexibility of the electrode. Thus, in conjunction with the low pitch, low diameter wire coil 26, the slug serves as a "heat sink", and also reducing the degree of tissue coagulation at the electrode site due to the minimization of current density at the electrode/tissue interface. More particularly, the distal end 36 of the slug 34 may present a surface area of between about 0.01 in$^2$ and 0.1 in$^2$, while the slug 34 may have a mass of about 1 gram to 10 grams.

With reference to FIG. 4, an electrode 46 according to the present invention is shown which includes a hand-piece 48 with an elongated shaft or catheter tubing 50 extending distally therefrom and terminating in a screw-type electrode 52 that extends beyond the distal end of the catheter tubing 50. The electrode 52 is adapted to be conductively connected to one of the outputs of an RF generator (such as the generator 20 shown in FIG. 1) by means of an insulated conductive cable 54 extending from the proximal end of the hand-piece 48. The hand-piece 48 includes a thumb wheel 56 rotatably secured to the distal end thereof and fixedly connected to the screw electrode 52 (by means including the conductive wire or other drive member not shown) for rotating the electrode 52 with respect to the catheter tubing, thus facilitating screw attachment of the electrode 52 to the heart wall.

To facilitate the steering or guiding of the catheter 50/electrode 52 during a minimally-invasive procedure, any well-known structure may be employed. As illustrated, a wire 58 may be secured to the catheter tubing 50 so as to extend between the distal end of the tubing 50 and a thumb lever 60 rotatably mounted to the hand-piece 48. Actuation of the thumb lever 60 selectively extends or retracts the wire 58 to steer the distal end of the catheter tubing 50, as indicated by the double-headed arrow 62. Thus, a pair of devices such as that shown in FIG. 4 could be introduced through small incisions and positioned on the heart wall using the thumb lever 60 to steer the electrode 52 to the desired position and the thumb wheel 56 to screw the electrode 52 to the heart wall.

When used for ablating cardiac tissue, it is desirable that the conductive screw 26 of the electrode penetrate as much of the thickness of the cardiac tissue as possible, without completely puncturing the heart wall and protruding into the interior or exterior of the heart. With reference to FIG. 5, to this end, each electrode may also include an EKG wire 38 extending through the outer insulating member 28 and terminating in a tip 40 that extends distally beyond the distal-most portion of the conductive screw 26. (For purposes of clarity, the slug 34 is not shown in the embodiment of FIG. 5. However, the spiral of the conductive coil encircles the slug at the distal end of the insulating member 28 while, in the embodiment employing a slug, the EKG wire 36 may extend through a central hole in the conductive slug 34.) The structure shown in FIG. 3 could also be used to provide for a bipolar EKG, in which case wire 38 with its exposed tip 40 would be connected to a first EKG and the coiled wire 30 connected to a second EKG.

The EKG wire 38 is preferably covered by an insulating material, except for the distal tip 40, which is free of insulation. This permits the EKG reading to be taken only at the very tip of the EKG wire. Accordingly, as the electrode is screwed into the heart tissue, the electrode and EKG wires advance simultaneously. As the electrode wire passes out of the myocardium and penetrates the epicardium, the EKG reading abruptly decreases or disappears, thus signaling to the cardiologist or electrophysiologist that the conductive screw has penetrated nearly the entire tissue thickness. As noted above, an alternative arrangement provides an EKG sensor on the distal end of the electrode 26 so that the physician can immediately detect piercing of the heart wall by the electrode. Alternatively, more than two electrodes may be used to form two or more ablation segments simultaneously.

Figure 6:
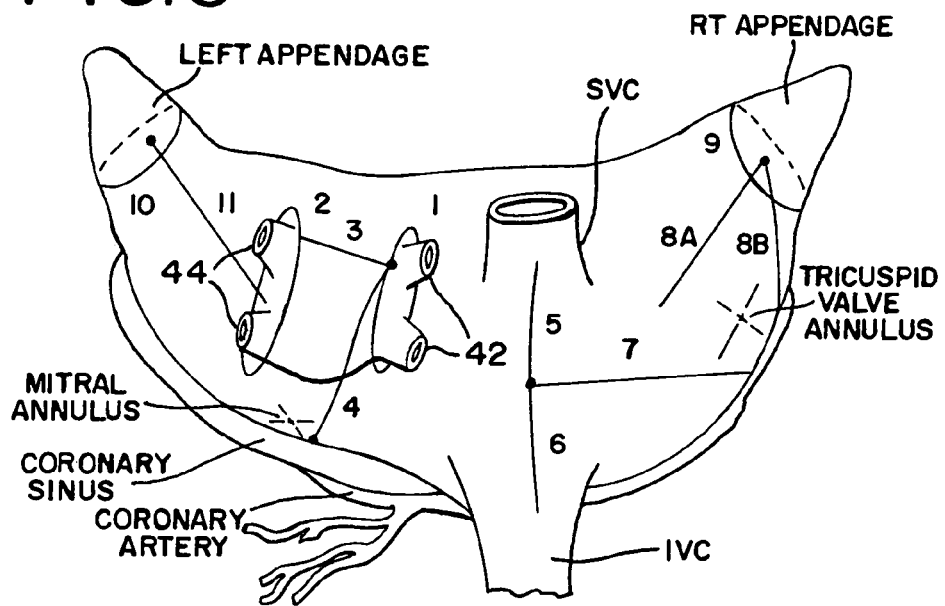
FIG. 6 is a top view of a human heart showing a series of ablation lines that comprise a type of Maze procedure.

The low-pitch electrodes of the present invention can be used to make the series of lesions commonly associated with the Maze procedure. With reference to FIG. 6, there is seen a posterior view of a heart showing a series of lesions 1-11 that may be made when performing the Maze procuedure. The electrodes of the present invention may be used to make one or more of these lesions from the interior of the heart, which may be relatively easier to access than the exterior surface. However, the procedure can be performed on the exterior surface as well. The procedure will be described with respect only to the creation of lesion 1, which encircles the right pair of pulmonary veins, lesion 2, which encircles the left pulmonary veins, and lesion 3, which connects lesions 1 and 2. Each of these lesions may be made in a series or sequence of steps in which the electrodes are attached to the heart and activated to form a first lesion segment. Then one of the electrodes is "unscrewed" and moved step-wise, or "leap-frogged", with respect to the other electrode. The electrodes are then activated again to form a second lesion segment connected to the first, and the steps repeated again a sufficient number of times to complete the desired lesion. Alternatively more than two electrodes may be used to form two or more ablation segments simultaneously.

Figure 7:
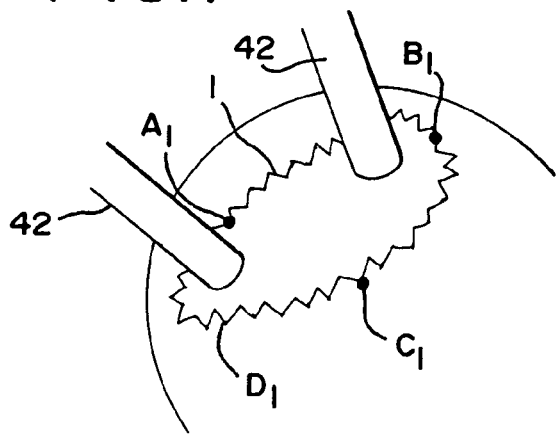
FIG. 7 is a schematic view of a pair of pulmonary veins illustrating the process of making a continuous ablation line that circumscribes a pair of veins.

With reference to FIG. 7, a schematic representation of the right pulmonary veins 42 is shown. The lesion 1 is created by attaching one of the electrodes 12, 14 to location $A_1$ and the other to location $B_1$, and activating the electrode to form a lesion between locations $A_1$ and $B_1$. Typically, the electrodes can be placed from 1 to 4 cm apart to provide a satisfactory transmural lesion between the electrodes. For example, the electrodes may be positioned about 2 cm (20 mm) apart, and a current flow therebetween of about 1 ampere (1000 milliamperes) could be employed to create a line of ablation therebetween. Then the electrode from location $A_1$ is moved to location $C_1$, the electrodes activated, thus forming the lesion between points $B_1$ and $C_1$. Then the electrode from point $B_1$ is moved to location $D_1$ and the electrodes activated to form the lesion between points $C_1$ and $D_1$. Then the electrode from location $C_1$ is moved to location $A_1$ and the electrodes activated to make the lesion from location $D_1$ to location $A_1$, thus completely encircling the right pulmonary veins with lesion number 1.

Figure 8:
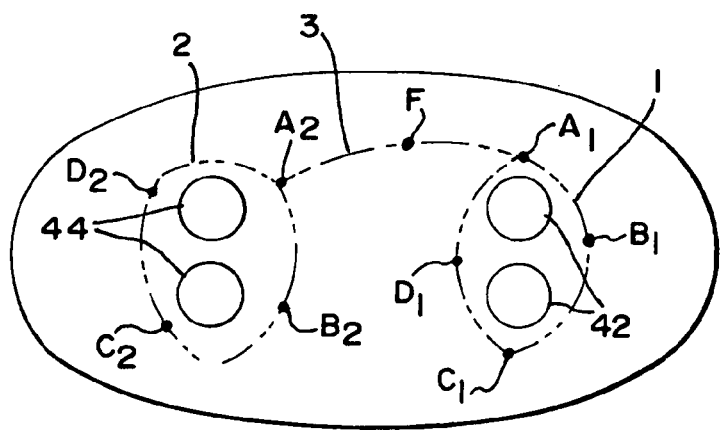
FIG. 8 is a schematic view of two pairs of pulmonary veins illustrating the process for making a series of ablation lines that circumscribe each pair of pulmonary veins and connect the circumscribing ablation lines.

Then, with reference to FIG. 8, lesion 2 may be made in a similar fashion about the other pair of pulmonary veins 44 by moving the electrodes serially from locations $A_2$-$D_2$, and activating the electrodes in the same manner as described above with respect to the formation of lesion 1. Once the pulmonary veins 44 are encircled by lesion 2, the electrode from location $D_2$ can be moved to location F and then activated to make the lesion $A_2$-F. Then the electrode from location $A_2$ can be moved to location $A_1$ and then activated to make the lesion connecting F with $A_1$, thus completing lesion 3, and connecting lesions 1 and 2. As noted above, the other lesions required for the Maze or other cardiac procedures can be made in a similar step-wise fashion.

With the present invention, it is contemplated that a lesion line of about 100 mm could be made with about seven lead placements. While this may seem laborious, it is a relatively easy procedure to employ, which forms a reliable lesion line even with the movement of a beating heart, and without the trauma, cost and recovery of an open heart Maze procedure.

The invention claimed is:

1. A method of forming a transmural lesion in cardiac tissue so as to encircle at least a pair of pulmonary veins comprising:
   a) positively securing a first electrode to the cardiac tissue at a first location;
   b) positively securing a second electrode to cardiac tissue at a second location spaced from the first location;
   c) connecting the electrodes to opposite poles of a bipolar RF generator;
   d) energizing the electrodes to ablate cardiac tissue between the electrodes between the first and second locations;
   e) moving the first electrode and positively securing the first electrode to cardiac tissue at a third location spaced from the second location;
   f) energizing the electrodes to ablate cardiac tissue between the electrodes between the second and third locations;
   g) moving the second electrode and positively securing the second electrode to cardiac tissue at a fourth location spaced from the third location;
   h) energizing the electrodes to ablate cardiac tissue between the electrodes between the third and fourth locations; and
   i) repeatedly alternately moving the first and second electrodes and energizing the electrodes until a lesion encircling the pulmonary veins is completed.

2. The method of claim 1 in which at least one of the electrodes is shaped to provide a sufficiently low current density in the vicinity of the electrode to avoid substantial tissue desiccation when energized.

3. The method of claim 1 in which at least one of the electrodes is generally spiral-shaped.

4. The method of claim 3 in which the spiral-shaped electrode has a pitch between about two coils per millimeter of axial length to about three coils per five millimeters of axial length.

5. The method of claim 3 in which the spiral-shaped electrode has a diameter between about two to five millimeters.

6. The method of claim 1 in which the cardiac tissue is the myocardium and at least one electrode does not extend completely through the myocardium.

7. The method of claim 1 including an EKG sensor associated with at least one of the electrodes and located distal of the electrode.

* * * * *